United States Patent [19]

Doonan et al.

[11] 4,374,985

[45] Feb. 22, 1983

[54] HYDRATED ALKALI METAL DICHLOROISOCYANURATE AND ITS PRODUCTION

[75] Inventors: David F. Doonan, Lake Charles; Noel N. Coe, Westlake, both of La.

[73] Assignee: Olin Corporation, New Haven, Conn.

[21] Appl. No.: 27,349

[22] Filed: Apr. 5, 1979

[51] Int. Cl.³ .......................................... C07D 251/36
[52] U.S. Cl. ...................................................... 544/190
[58] Field of Search ......................................... 544/190

[56] References Cited

U.S. PATENT DOCUMENTS

| | | | |
|---|---|---|---|
| 3,818,002 | 6/1974 | Goelz et al. | 544/190 |
| 3,951,972 | 4/1976 | Nelson et al. | 260/248 |
| 4,005,087 | 1/1977 | Saeman | 544/190 |
| 4,182,871 | 1/1980 | Moller | 544/190 |

*Primary Examiner*—John M. Ford
*Attorney, Agent, or Firm*—Donald F. Clements; James B. Haglind

[57] ABSTRACT

Hydrated alkali metal dichloroisocyanurate particles are prepared in a process which comprises, in a first step, spraying droplets of an aqueous slurry of alkali metal dichloroisocyanurate into an evaporation zone fed with a moving stream of heated gas to evaporate water from the droplets and form dry porous solid spherical particles of hydrated sodium dichloroisocyanurate. In a second step, the dry particles are fluidized in a cooling gas until cooled to a temperature below about 50° C. The resulting porous hydrated particles have a uniform distribution of hydration, are dust-free, and quickly dissolve in water.

26 Claims, 1 Drawing Figure

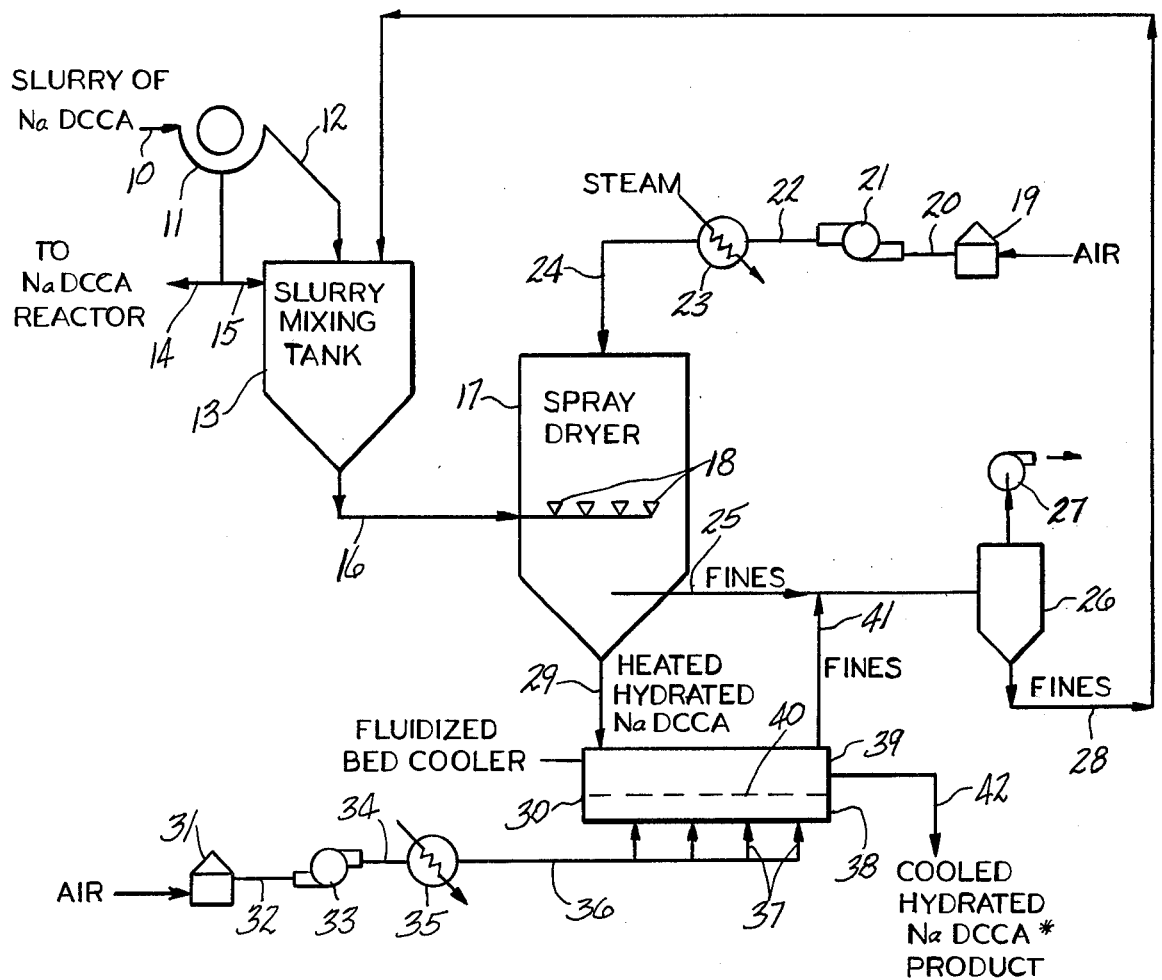

HYDRATED ALKALI METAL DICHLOROISOCYANURATE AND ITS PRODUCTION

This invention relates to novel alkali metal dichloroisocyanurates and the process for preparing them.

Alkali metal dichloroisocyanurates have been used extensively in water treatment processes and in the preparation of sanitizing cleansing agents. Generally these compounds are prepared by subjecting particles of a wet cake or aqueous slurry of alkali metal dichloroisocyanurate to one of a variety of drying techniques. In the flash drying technique, particles of wet cake are subjected to elevated temperatures to effect rapid evaporation of water. The resulting solid anhydrous particles are extremely fine and must be compacted and then milled in order to produce a useful granular form of the alkali metal dichloroisocyanurate.

In the fluidized bed technique, which employs beaters to prevent the formation of lumps of wet cake, the particles are of satisfactory size, but the prolonged contact of the wet particles with the heated atmosphere results in a substantial loss of available chlorine from the particles.

The spray graining technique produces particles of uniform size, but the rate of solubility is a relatively low one, and below that of alkali metal dichloroisocyanurates produced by other techniques. Although the spray graining technique produces anhydrous particles of desired size, the hydrated particles which are prepared by this technique have undesirable caking characteristics which are probably caused by the uneven distribution of water in the particles as hydrated water.

Hydrated alkali metal dichloroisocyanurates are not readily prepared by drying techniques presently available in the art. There is a need for an improved process for preparing hydrated alkali metal dichloroisocyanurates of relatively high purity, which are porous, substantially dust free, and rapidly dissolve in water.

It is an object of the present invention to provide hydrated alkali metal dichloroisocyanurate particles which are dust free, free-flowing, rapidly soluble in water and of extremely high purity.

Another object of the present invention is to provide an improved process for preparing hydrated sodium dichloroisocyanurate of uniform hydration distribution.

An additional object of the present invention is to provide a process for the production of hydrated alkali metal dichloroisocyanurate particles in which cooling of the particles is effected after drying.

Still a further object of the present invention is to provide novel hydrated sodium dichloroisocyanurate particles which are dust free, free-flowing, rapidly soluble in water and of extremely high purity.

These and other objects will be apparent from the following detailed description of the invention.

Briefly, the process of this invention comprises a first step of spraying droplets of an aqueous slurry of an alkali metal dichloroisocyanurate into an evaporation zone fed with a moving stream of gas heated to a temperature sufficiently high to evaporate water from the droplets and to form dry porous solid spherical particles of hydrated alkali metal dichloroisocyanurates. In a second step of the process, the resulting dry hydrated particles are fluidized in a cooling gas to reduce the temperature of the particles to below about 50° C. This cooling technique not only cools the particles to near ambient temperature, but also effects substantially uniform distribution of hydration throughout the particles. The resulting cooled particles are novel hydrated alkali metal dichloroisocyanurates particles which are porous, dust free, quick dissolving spheres of high purity.

The invention is described hereafter in terms of sodium dichloroisocyanurate, a preferred embodiment, for purposes of simplifying the description. However, those skilled in the art will recognize that the process and composition of this invention, as described below, also includes other alkali metal isocyanurates such as potassium isocyanurate and lithium isocyanurate.

The FIGURE shows in schematic form the details of a preferred embodiment of the process of this invention in which an aqueous slurry of sodium dichloroisocyanurate is spray dried, and the resulting heated hydrated particles are cooled in a fluidized bed.

In more detail, the FIGURE shows a slurry of sodium dichloroisocyanurate fed through slurry line 10 to filter 11, where the slurry is separated into a filter cake and a filtrate. The filter cake is conveyed through cake line 12 to slurry mixing tank 13. The filtrate is recycled through filtrate line 14 to the reactor used in the preparation of the sodium dichloroisocyanurate slurry, or otherwise disposed of. If desired, a portion of the filtrate may be conveyed through bleed line 15 to the slurry mixing tank 13 to adjust the water concentration of the slurry to the desired level.

The aqueous slurry is conveyed from slurry mixing tank 13 through dryer feed line 16 to spray dryer 17 where it is sprayed through nozzles 18, preferably in an upward direction.

Atmospheric air or other suitably inert gas is drawn into air filter 19 and through feed line 20 by means of blower 21. The clean air is conveyed through air line 22 to heat exchanger 23, where the temperature of the air is increased sufficiently to evaporate free water from the droplets of aqueous slurry of sodium dichloroisocyanurate. Heated air is conveyed through heated air line 24 to the top of spray dryer 17, where it passes as a moving stream of heated gas from the top of the dryer, across nozzles 18, and out of air discharge line 25.

The pressure applied by blower 21 is sufficient to convey the heated gas along this path and into cyclone 26, which separates any fine particles of sodium dichloroisocyanurate contained therein. Fines-free air is discharged from the top of cyclone 26 through discharge blower 27. Fines are collected in cyclone 26 and conveyed through fines recycle line 28 to slurry mixing tank 13.

When the moving stream of heated gas from heated air line 24 contacts the droplets of aqueous slurry of sodium dichloroisocyanurate discharged from nozzles 18, free water is evaporated from the droplets and dilutes and cools the heated air stream. The droplets, as a result of this drying technique, form heated porous solid spherical particles of hydrated sodium dichloroisocyanurate. There solids fall to the bottom of spray dryer 17, where they are discharged through heated hydrated sodium dichloroisocyanurate line 29. Any fines contained in the particles are withdrawn with the cooled air stream through air discharge line 25.

The heated hydrated solids are conveyed through line 29 to the top of fluidized bed cooler 30, which is fed with cooled gas such as air. The air is conveyed through air filter 31, through air feed line 32 by means of blower 33 through air line 34 to heat exchanger 35. In heat exchanger 35, the temperature of the air is adjusted to a temperature sufficient to reduce the temperature of the heated hydrated particles to below about 50° C. The cooled gas is fed through cooled gas line 36 to manifold ports 37 and into the bottom portion 38 of fluidized bed cooler 30.

Heated hydrated particles from line 29 are conveyed to the upper portion 39 of fluidized bed cooler and collect on screen 40, which separates upper portion 39 from bottom portion 38. The openings in screen 40 are sufficiently large to permit the passage of cooling gas into upper portion 39 but sufficiently small to prevent the passage of the heated hydrated particles into bottom portion 38.

The cooled air passes from manifold ports 37 through bottom portion 38, through the openings in screen 40 into the upper portion 39 where it contacts the heated hydrated particles and passes through spent air exit 41. Upon contact with the heated hydrated particles, there is a transfer of energy between the gas and solids. Motion is imparted to the particles by the gas, which lifts the particles above screen 40 and conveys them to particle exit 42. While traveling this path, a thermal transfer between the cooling gas and particles occurs at a rate sufficient to reduce the temperature of the particles to below about 50° C. In addition, a hydration equilibrium is imparted to the particles to produce dry cooled porous solid spherical particles of hydrated sodium dichloroisocyanurate. These particles are discharged through particle exit 42, and conveyed to packaging or storage (not shown). As the cooled gas contacts the heated particles in fluidized bed cooler 30, any fines remaining in the particles are carried with the spent gas through spent air exit line 41 for further processing. The spent gas stream in 41 is combined with the contents of air discharge line 25, as shown in the FIGURE and conveyed to cyclone 26. If desired, the spent gas and fines may be fed directly to cyclone 26 or another cyclone if desired.

In carrying out the process of this invention, an aqueous slurry of sodium dichloroisocyanurate is prepared by any convenient technique. For example, U.S. Pat. Nos. 3,035,056 and 3,035,057, which issued on May 15, 1962 to William F. Symes and William F. Symes et al, respectively, describe the preparation of sodium dichloroisocyanurate from chlorine and trisodium isocyanurate. However, any convenient technique for preparing aqueous slurries of sodium dichloroisocyanurate may be employed. Generally slurries produced by these techniques have a solid content below about 40% by weight. In order to prepare a suitable slurry feed for spray dryer 17, any pumpable, sprayable slurry containing greater than about 40% by weight of sodium dichloroisocyanurate is employed. The solids content is preferably increased to a range from about 50 to about 60 percent, and more preferably from about 56 to about 58%, by filtration, centrifuging, or any other suitable technique.

The aqueous slurry having a concentration within these ranges is fed to spray dryer 17 by pumping the aqueous slurry at suitable pressures through nozzles 18 by a suitable pumping means (not shown). Pumping pressures in the range from about 200 to about 500 and preferably from about 225 to about 275 pounds per square inch are employed. However, higher or lower pressures may be employed if desired.

Suitable spray dryers include those employing single fluid nozzles, two or more fluid nozzles, and wheel atomizers. Single fluid nozzles are preferred. Nozzles employed are those having openings, for example, of from about 0.5 to about 5.0 and preferably from about 1.0 to about 3.0 millimeters. The sodium dichloroisocyanurate slurry may be sprayed from nozzles positioned in any suitable location in the dryer such as the upper part or the lower part. In a preferred embodiment, the nozzles are located in the lower part of the dryer and the slurry sprayed upward in the manner of a fountain.

After the slurry has left the nozzles as droplets and the droplets are contacted with the moving bed of heated gas, porous solid spherical particles of the sodium dichloroisocyanurate hydrate are formed. The heated gas is any inert gas such as air, nitrogen, carbon dioxide, or the like. The temperature of the heated gas fed through heated air line 24 is generally in the range from about 170° to about 250° C. and preferably in the range from about 185° to about 220° C. The particles are dried to a spherical form having the desired degree of hydration by controlling the temperature of the moisture-bearing gas leaving the spray dryer. The outlet temperature of this gas is maintained, for example, in the range of from about 100° to about 150° C. and preferably from about 100° to about 110° C. by controlling the gas inlet temperature. The heated particles having free water removed are discharged from the spray dryer after an average residence time of from about 10 to about 60 seconds and preferably from about 15 to about 30 seconds of elapsed time from the time when the slurry is sprayed until the time when the solid dired particles are removed from the dryer.

The heated sodium dichloroisocyanurate hydrate particles removed from spray dryer 17 are fed to the upper portion 39 of fluidized bed cooler 30 at a temperature in the range from about 50° to about 100° C., and preferably from about 70° to about 80° C.

Any suitable fluid bed cooler may be used for cooling the heated particles. A preferred fluid bed cooler is one having a vibrating screen means for agitating and conveying the particles. As the heated particles are fed to upper portion 39, they are contacted with cooling gas which passes through opening in screen 40. The cooling gas is any suitable inert fluidizing gas such as air, nitrogen, or carbon dioxide. The cooling gas is fed at a temperature lower than the feed temperature of the dried particles. To obtain the desired degree of cooling, gas temperatures in the range from about 15° C. to about 50° C. are quite satisfactory when gas velocities of from about 0.1 to about 0.6, preferably from about 0.2 to about 0.5, and more preferably from about 0.3 to about 0.4 meters per second are used. At these gas velocities, sufficient contact to effect the desired degree of cooling is obtained without blowing an excessive amount of solids out of spent air exit 41.

In another embodiment of the invention two zones of cooling are employed in fluidized bed cooler 30. In the first zone, which comprises from about ⅓ to about ½ of the bed area, conditioned air at a temperature in the range from about 30 to about 100 and preferably from about 40° to about 50° C. is fed through manifold ports 37 at the feed end of fluidized bed cooler 30. In the second zone, which comprises from about ½ to about ⅔ of the bed area, conditioned air at a temperature in the range from about 20 to about 40 and preferably from about 25° to about 35° C. is fed through manifold ports 37 at the discharge end of fluidized bed cooler 30.

To produce a cool, dry product having the desired amounts of water of hydration in either cooling embodiment, the relative humidity of the fluidizing cooling gas

COMPARATIVE TEST C

The solubility rate of the product of this invention, such as the product produced in the above EXAMPLE, was compared with the solubility rate of commercial sodium dichloroisocyanurate dihydrate prepared by the conventional flash drying-compaction technique of the type described in COMPARATIVE TEST B.

A four foot high, water filled glass tube was employed in measuring the solubility rate. Three samples, identified as Samples 1, 2, and 3 were tested in the above glass tube. These samples were identified as follows:

Sample 1—the product of the above EXAMPLE of this invention having the screen size of the above EXAMPLE.

Sample 2—commercial sodium dichloroisocyanurate dihydrate prepared by flash drying and compaction, and having one percent by weight of particles with a diameter of +840 microns.

Sample 3—a fraction of commercial sodium dichloroisocyanurate dihydrate prepared by flash drying and compaction wherein the fraction is essentially all −600 microns, with about 4.5 percent −150 microns, which corresponds closely to the particle size of Sample 1.

A small portion of each sample was separately placed into the above-identified glass tube filled with fresh water to a depth of 4 feet and the distance from the top of the water level to the level required to dissolve all of the sample was measured. Sample 1, a product of this invention, was dissolved in a distance of less than ¼ inch from the top of the column. Sample 2, which is a presently available commercial product, did not completely dissolve until the particles had reached a depth of 26 inches.

Sample 3, which is a commercial product screened to conform closely to the particle size of Sample 1 required a depth of 3 inches to completely dissolve.

From these data, it can be seen that the product of this invention dissolves almost immediately after contact with the water, while the unscreened compacted commercial product required a depth of 26 inches to achieve complete solubility. Such a large distance may permit agglomeration and caking of particles in the water being treated. In contrast, the product of this invention is dissolved before such agglomeration can occur. In addition, the commercial product screened to recover a fraction corresponding in size to the product of this invention, required a depth of 3 inches to dissolve. This comparative test showed that the product of this invention is more porous and more soluble than the compacted material prepared by a conventional flash drying-compaction technique.

What is claimed is:

1. A process for preparing dry cooled porous particles of hydrated alkali metal dichloroisocyanurate which comprises:
   a. spraying droplets of an aqueous slurry of solid alkali metal dichloroisocyanurate into an evaporation zone fed with a moving stream of gas heated to a temperature sufficiently high to evaporate free water from the droplets and form from said droplets heated porous solid spherical particles of hydrated alkali metal dichloroisocyanurate containing from about 7 to about 14 percent by weight of water of hydration,
   b. fluidizing said heated particles in a cooling fluidizing gas until said particles are cooled to a temperature below about 50° C., and
   c. recovering the resulting dry cooled porous solid spherical particles of hydrated alkali metal dichloroisocyanurate produced thereby.

2. The process of claim 1 wherein said aqueous slurry of alkali metal dichloroisocyanurate contains from about 50 to about 60 percent by weight of said solid alkali metal dichloroisocyanurate.

3. The process of claim 2 wherein said slurry of alkali metal dichloroisocynaurate has a solid content in the range from about 56 to about 58 percent by weight of solid alkali metal dichloroisocyanurate.

4. The process of claim 3 wherein said fluidizing gas is selected from the group consisting of air, nitrogen, and carbon dioxide.

5. The process of claim 4 wherein said heated particles are fed to a fluidized bed cooler at a temperature in the range from about 50° to about 30° C.

6. The process of claim 5 in which said fluidizing gas is at a temperature in the range from about 15° to about 50° C., and has a relative humidity in the range from about 25 to about 50 percent.

7. The process of claim 6 in which said cool, dry particles of hydrated alkali metal dichloroisocyanurate recovered from said fluidized bed cooler are at a temperature in the range from about 30° to about 40° C.

8. The process of claim 7 wherein said alkali metal dichloroisocyanurate is sodium dichloroisocyanurate.

9. The process of claim 8 wherein said moving stream of gas is fed to said evaporation zone at a temperature in the range from about 170° to about 250° C., and after contacting said droplets, said gas is withdrawn from said evaporation zone at a temperature in the range from about 100° to about 150° C., said heated porous solid spherical particles of hydrated alkali metal dichloroisocyanurate formed having a residence time in said evaporation zone of from about 10 to about 60 seconds.

10. The process of claim 9 wherein said moving stream of gas is fed to said evaporation zone at a temperature within the range from about 185° and about 220° C., and after contacting said droplets, said gas is withdrawn from said evaporation zone at a temperature in the range from about 100° to about 110° C.

11. The process of claim 10 wherein said fluidizing gas is air.

12. The process of claim 11 wherein the retention time for said sodium dichloroisocyanurate product in said fluidized bed cooler is in the range from about 2 to about 20 minutes.

13. The process of claim 11 wherein the velocity of said fluidizing gas is from about 0.2 to about 0.5 meters per second.

14. The process of claim 12 wherein said hydrated sodium dichloroisocyanurate product recovered from said fluidized bed cooler is at a temperature in the range from about 30° to about 40° C.

15. The process of claim 13 wherein cooling of said particles in said fluidized bed cooler is effected in two separate zones, the first zone being fed with air at a temperature in the range from about 30° to about 100° C. and the second zone being fed with air at a temperature in the range from about 20° to about 40° C.

16. Porous spherical particles of hydrated sodium dichloroisocyanurate prepared by the process of claim 1 having a particle size in the range from about 100 to is controlled at a relatively constant level. While it will be recognized that by employing dry, fluidizing gases, some drying may be carried out in the fluid bed cooler. This is minimized by employing fluidizing cooling gases having a relative humidity of from about 25 to about 50, and preferably from about 30 to about 40 percent.

The fluidized bed cooler 30 is operated to provide a retention time of the solids in the fluidized bed of from about 2 to about 20, and preferably from about 5 to about 15 minutes. Free-flowing sodium dichloroisocyanurate hydrate particles having a temperature below about 50° C., and preferably in the range of about 30° to about 40° C., are removed from the fluidized bed cooler 30. These solids are porous solid spherical, dust-free particles of hydrated sodium dichloroisocyanurate which have a uniform distribution of water of hydration therein.

Particles of sodium dichloroisocyanurate hydrates having any desired water content may be produced by the process of the present invention, for example, those having a water of hydration content of from about 7 to about 14 percent by weight. In a preferred embodiment, sodium dichloroisocyanurate hydrate having a water content in the range of from about 12 to about 13.5 is produced.

Particle size of the cooled, dry hydrated product of this invention is in the range of from about 100 to about 420 microns and preferably from about 150 to about 330 microns in diameter.

Porous spherical particles produced by the process of the present invention have a low bulk density and are readily dissolved in water. The bulk density of sodium dichloroisocyanurate produced by conventional techniques ranges from about 55 to about 60 pounds per cubic foot.

However, bulk densities of products produced by the process of this invention are in the range of from about 30 to about 50, and preferably from about 40 to about 45 pounds per cubic foot. Particle bulk densities are determined by the American Standard for Testing Materials Method B527-70, Standard Test Method for Tap Density of Powders of Refractory Metals and Compounds by Tap-PAK Volumeter.

The novel spherical, porous particles of alkali metal isocyanurate produced by the novel process of the present invention are free-flowing, have no sharp edges, are dust-free, are readily soluble in liquids such as water, have a favorable bulk density and contain substantially uniform amounts of water of hydration.

In contrast, compacted alkali metal isocyanurates prepared by conventional prior art techniques are not porous, are not dust free, are not dissolved as easily in water and have a higher bulk density.

To further illustrate the process of the present invention, the following EXAMPLE is presented. All percentages are by weight unless otherwise specified.

EXAMPLE

An aqueous slurry containing 57 percent by weight sodium dichloroisocyanurate was pumped to a 2.7 meters in diameter, fountain-type spray dryer having a 1 millimeter diameter single-fluid nozzle at a rate of 300 lb./hr. The dryer air outlet temperature was controlled at about 105° C. by controlling the air inlet temperature at about 188° C. The water content of sodium dichloroisocyanurate hydrate particles coming from the dryer averaged 13.4 percent and the product temperature was 56° C. A sample of the spray dried product was recovered and screened. Moisture analysis of the screened fractions showed more water in coarse particles, which caused the product to cake.

The hot product was fed to a fluidized bed cooler (Niro Atomizer, Inc. Vibro-fluidizer) having a vibrating bed. The cooler was fed with air at 40° C., and a relative humidity of 50 percent with a velocity in the bed of 0.33 m./sec. The product had a final temperature of 40° C., a moisture content of 12.6 percent and consisted of porous spheres having the following particle size:

| Microns | % Retained |
| --- | --- |
| +420 | 4.1 |
| +250 | 53.2 |
| +177 | 29.0 |
| +149 | 9.0 |
| −149 | 4.7 |

During the cooling stage, product retention time in the fluid bed cooler was an average of about 5 minutes. The product recovered had a bulk density of about 41 pounds per cubic foot, an available chlorine content of about 54.9 percent and assayed at 97.8 percent sodium dichloroisocyanurate dihydrate. Analysis of screen fractions of the hydrated product showed the moisture content to be evenly distributed among the various screen fractions. The cooled product was found to be dust free and free-flowing with no evidence of caking.

COMPARATIVE TEST A

The procedure of the EXAMPLE was repeated except that the product of the spray dryer was not fed to the fluidized bed cooler, but instead was stored in a container under ambient conditions until room temperature was achieved. The product analysis was 12.7 percent H₂O and 55.8 percent available chlorine.

Upon cooling at ambient conditions, the product was observed to contain numerous soft clumps of particles up to 3 inches in diameter. In addition, pockets of chlorine were present in the mass, indicating product decomposition. These data show that when the fluidized bed cooler step is omitted from the process of this invention, large clumps of product are produced which decompose on standing.

COMPARATIVE TEST B

In accordance with a conventional, commercial technique, sodium dichloroisocyanurate filter cake containing 35 percent free and combined water was fed to a flash dryer by means of a screw feeder. A portion of the dried product from the flash dryer was recycled and blended with the wet cake in the screw feeder to prevent the wet cake from sticking. The flash dryer was operated with an air inlet temperature of 300° F. and an air outlet temperature of 140° F. The product had a moisture content of 12.6 percent, an available chlorine content of 55.4 percent. It was compacted between rolls to provide a product having a particle size distribution as follows:

| Screen Size | Percent by Weight |
| --- | --- |
| +420 microns | 2.0 |
| −420 +74 microns | 13.4 |
| −74 +44 microns | 15.4 |
| −44 microns | 69.2 | about 420 microns, and a water of hydration content of from about 7 to about 14 percent by weight.

17. The particles of claim 16 having a bulk density of from about 30 to about 50 pounds per cubic foot.

18. The particles of claim 17 wherein said particle size is from about 150 to about 330 microns.

19. The particles of claim 18 wherein the water of hydration content is from about 12 to about 13.5 percent by weight.

20. A process for cooling heated particles of an alkali metal dichloroisocyanurate which comprises:
   a. feeding heated particles of a hydrated alkali metal dichloroisocyanurate containing from about 7 to about 14 percent by weight of water of hydration into a fluidized bed cooler, contacting said hot particles with a cooling fluidizing gas having a temperature in the range from about 15° to about 50° C., and having a relative humidity in the range from about 25 to about 50 percent, and
   b. recovering cooled particles of alkali metal dichloroisocyanurate product from said fluidized bed cooler.

21. The process of claim 20 in which said fluidizing gas is selected from the group consisting of air, nitrogen, and carbon dioxide.

22. The process of claim 21 wherein said cooled particles of alkali metal dichloroisocyanurate recovered from said fluidized bed cooler are at a temperature in the range from about 30° to about 40° C.

23. The process of claim 22 wherein said heated particles are introduced into said fluidized bed cooler at a temperature in the range from about 50° to about 80° C.

24. The process of claim 23 wherein said alkali metal dichloroisocyanurate is sodium dichloroisocyanurate.

25. The process of claims 5, 14 or 24 wherein said particles are agitated while cooling in said fluidized bed cooler.

26. The process of claim 22 wherein cooling of said particles in said fluidized bed cooler is effected in two separate zones, the first zone being fed with air at a temperature in the range from about 30° to about 100° C. and the second zone being fed with air at a temperature in the range from about 20° to about 40° C.

* * * * *

UNITED STATES PATENT AND TRADEMARK OFFICE
CERTIFICATE OF CORRECTION

PATENT NO. : 4,374,985

DATED : February 22, 1983

INVENTOR(S) : David F. Doonan and Noel N. Coe

It is certified that error appears in the above-identified patent and that said Letters Patent is hereby corrected as shown below:

Column 4, line 29, delete "dired" and insert --dried--.

Column 8, Claim 5, line 3, delete "30°" and insert --80°--.

Signed and Sealed this

Nineteenth Day of April 1983

[SEAL]

Attest:

GERALD J. MOSSINGHOFF

Attesting Officer    Commissioner of Patents and Trademarks